United States Patent [19]

Mueller

[11] 4,153,590

[45] May 8, 1979

[54] PERFLUOROALKYL SUBSTITUTED ANHYDRIDES AND POLYACIDS, AND DERIVATIVES THEREOF

[75] Inventor: Karl F. Mueller, New York, N.Y.

[73] Assignee: Ciba-Geigy Corporation, Ardsley, N.Y.

[21] Appl. No.: 828,461

[22] Filed: Aug. 29, 1977

Related U.S. Application Data

[62] Division of Ser. No. 646,689, Jan. 5, 1976, Pat. No. 4,058,537.

[51] Int. Cl.$^2$ .............................. C08L 63/00
[52] U.S. Cl. .................. 260/29.2 EP; 260/13;
260/29.2 R; 260/29.2 M; 260/29.2 TN;
260/29.2 UA; 260/29.2 N; 260/29.2 E;
260/29.4 R; 260/29.6 R; 260/29.6 MQ;
260/29.6 MN; 260/29.7 SQ; 260/29.7 NQ;
260/29.7 N; 528/88; 528/90; 528/93
[58] Field of Search ................. 260/29.2 EP, 830 R, 260/2 EA

[56] References Cited

U.S. PATENT DOCUMENTS

| | | | |
|---|---|---|---|
| 3,284,383 | 11/1966 | Proops | 260/830 R |
| 3,711,514 | 1/1973 | Quick | 260/346.3 |

*Primary Examiner*—J. Ziegler
*Attorney, Agent, or Firm*—Luther A. R. Hall

[57] ABSTRACT

This invention describes new perfluoroalkyl substituted esters, diesters and polyesters which contain at least one cyclic 5-membered anhydride group or two carboxy groups, as well as half amides and half esters thereof; their synthesis and their use as surface-active reactants in polycondensate resin systems.

The anhydrides are synthesized by reaction of perfluoroalkyl substituted alcohols or diols with dianhydrides or an anhydrides-acid chloride and have the general structure

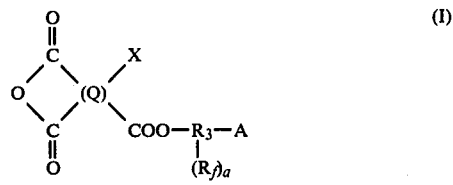

wherein:
Q is the tetra-radical rest of a tri- or tetracarboxylic acid, which contains at least one 1,2-dicarboxy grouping,
X is hydrogen or COOH,
R$_f$ is a perfluoroalkyl or perfluoroalkoxyperfluoroalkyl group of 4 to 18 carbon atoms,
a is 1 or 2,
A is hydrogen or

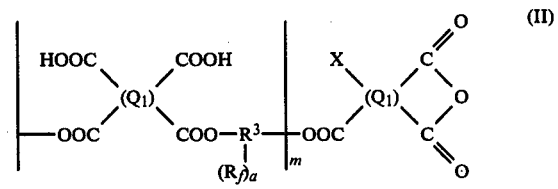

wherein:
m is an integer from 0 to 5, and
R$^3$ is the residue of a R$_f$ substituted alcohol or diol.

9 Claims, No Drawings

PERFLUOROALKYL SUBSTITUTED ANHYDRIDES AND POLYACIDS, AND DERIVATIVES THEREOF

The present application is a divisional of application Ser. No. 646,689, filed Jan. 5, 1976, now U.S. Pat. No. 4,058,537, issued Nov. 15, 1977.

BACKGROUND OF THE INVENTION

Perfluoroalkyl substituted compounds are widely used in a large number of applications where the unique ability of perfluoroalkyl groups to lower the surface energy of solids, or organic or aqueous solutions, is of decisive importance. In polymers, the presence of perfluoroalkyl groups reduces the polymer surface-free energy to below 15 dynes/cm, and such polymers are used by the textile industry to make fabrics not only water repellent, but also oil repellent.

$R_f$-surfactants which are otherwise like their hydrocarbon analogues in that they are either anionic, cationic, nonionic or amphoteric, but which contain perfluoroalkyl groups reduce the surface tension of aqueous or organic liquids to extremely low levels, down to 15 dynes/cm, as compared to 25–30 dynes/cm obtainable with conventional surfactants. Such low surface tensions allow these liquids, which may be molten polymers or polymer solutions or emulsions, to wet substrates which are otherwise impossible to wet. Therefore properties which depend on good wetting are often substantially improved, such as adhesion and surface smoothness, and such coating deficiencies as crawling, "fisheyes," "orange peel," etc. are largely eliminated. Numerous $R_f$-surfactants have been described in U.S. Pat. Nos. 2,915,554; 3,274,244; 3,621,059; 3,668,233; and German Offenlegungsschift No. 2,215,388.

$R_f$-surfactants of the prior art cited above are used for coating systems to help in wetting and to prevent crawling and other side effects of poor coatings. These $R_f$-surfactants are nonionic in nature because ionic compounds are poorly compatible with resins. All the $R_f$-surfactants described are non-reactive.

DETAILED DISCLOSURE

This invention pertains to new perfluoroalkyl substituted esters, diesters and polyesters which contain at least one cyclic 5-membered anhydride group or two carboxy groups as well as half amides and half esters derived therefrom and the processes to prepare said compounds.

The compounds of this invention are useful as surface-active reactants in polycondensation resin systems. The compounds of this invention contain chemical groups which can co-react with curable resin systems during the curing cycle. This assures optimum compatibility of the compounds of this invention as additives with the curable resin throughout the curing cycle. The perfluoroalkyl compounds may by themselves have minimal surface activity properties, but form surface active derivatives during cure of the resin in situ. Besides the optimal compatibility and effectiveness achieved, the perfluoroalkylated compounds of this invention are tightly built into the resin network and remain an integral part of it. They cannot bleed out, like other surfactants. This is an important and requisite property for coatings coming in contact with food. Additionally, the surface appearance of the coating is improved and often its surface free energy is reduced.

In specific detail, the compounds of this invention comprise perfluoroalkyl substituted esters of the formula I

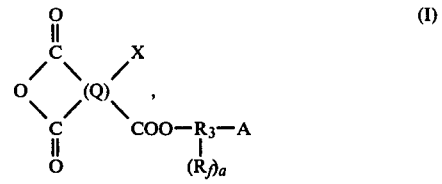

wherein

Q is the tetraradical rest of a tricarboxylic or tetracarboxylic acid which contains at least one 1,2-dicarboxy grouping, X is hydrogen or carboxy, $R_f$ is perfluoroalkyl of 4 to 18 carbon atoms or perfluoroalkoxyperfluoroalkyl of 4 to 18 carbon atoms, a is 1 or 2, A is hydrogen or the group II

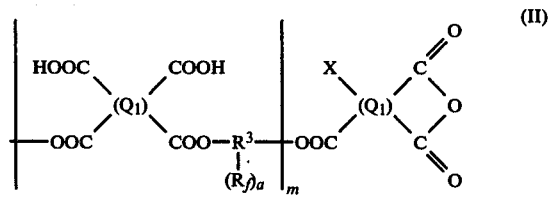

m is an integer from 0 to 5, $Q_1$ is the same as Q or is a different tetraradical rest of the definition given for Q, and $R^3$ is the residue of a $R_f$ substituted, branched or straight chain, aliphatic alcohol or diol of 1 to 12 carbon atoms which may contain 1 to 5 non-terminal oxygen, sulfur or nitrogen atoms, the third substituent on the nitrogen atoms being independently hydrogen, alkyl of 1 to 6 carbon atoms or hydroxyalkyl of 2 to 6 carbon atoms.

The preferred compounds of this invention are those of formula I wherein Q is the tetraradical rest of a tricarboxylic or tetracarboxylic acid selected from the group consisting of trimellitic acid, 3,3',4,4'-benzophenonetetracarboxylic acid, 1,2,4,5-benzenetetracarboxylic acid, 2,3,4,5-tetrahydrofurantetracarboxylic acid and

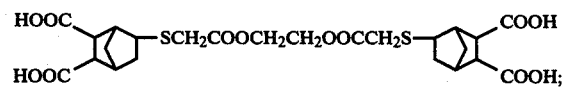

X is hydrogen or carboxy;

$R_f$ is perfluoroalkyl of 6 to 18 carbon atoms;

a is 1 or 2;

A is hydrogen or Group II

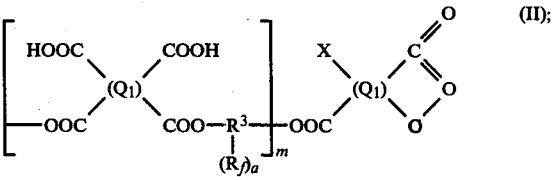

m is an integer from 0 to 2;

$Q_1$ is the same as Q; and $R^3$ is the residue of a $R_f$ substituted, aliphatic alcohol or diol of the structure

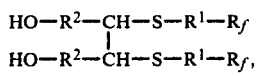
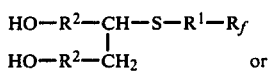

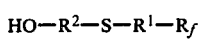 or $$HO-R^2-S-R^1-R_f$$

where $R^1$ is a branched or straight chain alkylene of 1 to 12 carbon atoms, alkylenethioalkylene of 4 to 12 carbon atoms, alkyleneoxyalkylene of 4 to 12 carbon atoms or alkyleneiminoalkylene of 4 to 12 carbon atoms where the nitrogen atoms contains as the third substituent hydrogen or alkyl of 1 to 6 carbon atoms; and $R^2$ is a straight or branched chain alkylene of 1 to 12 carbon atoms or an alkylenepolyoxyalkylene of the formula $C_nH_{2n}(OC_kH_{2k})_r$ where n is 1 to 12, k is 2 to 6 and r is 1 to 40.

Especially preferred compounds of this invention are those of formula I wherein Q is the tetraradical rest of tetracarboxylic acid selected from the group consisting of 2,3,4,5-tetrahydrofurantetracarboxylic acid and 3,3',4,4'-benzophenonetetracarboxylic acid; X is carboxy; $R_f$ is perfluoroalkyl of 6 to 18 carbon atoms; a is 1 or 2; A is group II

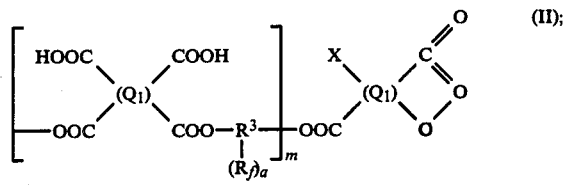

m is 0; $Q_1$ is the same as Q; and $R^3$ is the residue of an $R_f$ substituted aliphatic alcohol or diol of the structure

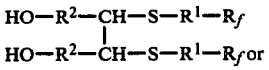
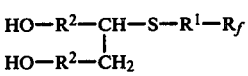

where $R^1$ is a branched or straight chain alkylene of 1 to 4 carbon atoms; and $R^2$ is a branched or straight chain alkylene of 1 to 4 carbon atoms or alkylenepolyoxyalkylene of the formula $C_nH_{2n}(OC_kH_{2k})_r$ where n is 1 to 4, k is 2 to 4 and r is 1 to 20.

Most preferably the compounds of this invention are those where $R_f$ is perfluoroalkyl of 6 to 18 carbon atoms, $R^1$ is ethylene; and $R^2$ is methylene or methyleneoxyalkylene of the formula $CH_2(OC_kH_{2k})_r$ where k is 2 and r is 1 to 20.

The perfluoroalkyl substituted alcohols or diols useful in this invention have the general structure

where Z is hydrogen or hydroxy. When Z is hydrogen in formula III, A in Formula I is also hydrogen. When Z is hydroxy, A in formula I has the structure of group II. $R^3$, a, and $R_f$ are as previously defined.

When Z is hydrogen and a is 1, other perfluoroalkyl alcohols contemplated to be of value in this invention include

  m = 1 to 12

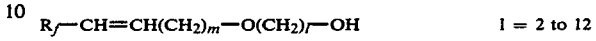  l = 2 to 12

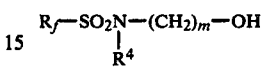

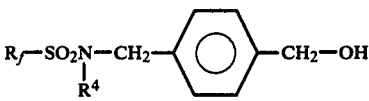

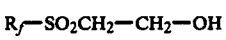

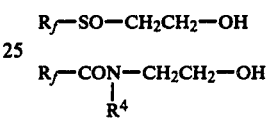

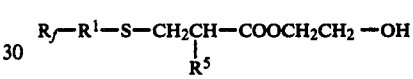

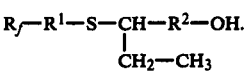

$$R_f-R^1-SCH_2CH_2O(CH_2)_4OH$$

$R_f-R^1-S(CH_2)_mOH$  m = 1 to 12

Where Z is hydroxy and a is 1, other perfluoroalkyl diols contemplated to be of value in this invention have the structures below

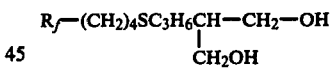

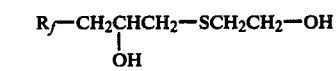

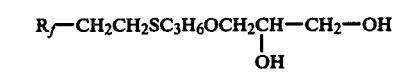

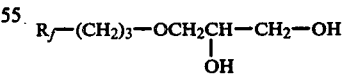

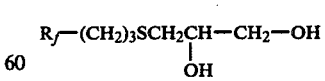

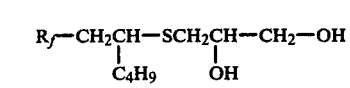

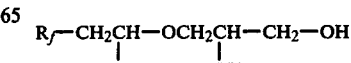

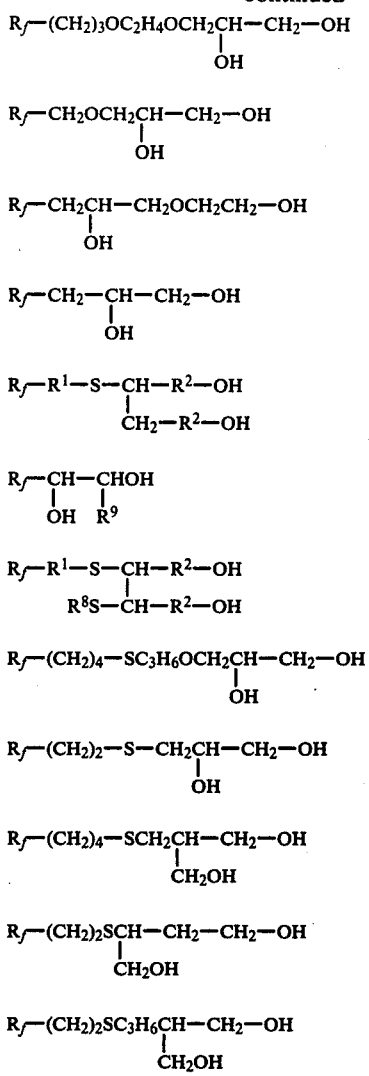

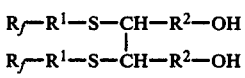  (Z = OH)

$(R_f CH_2CH_2)_2 C(CH_2OH)_2$

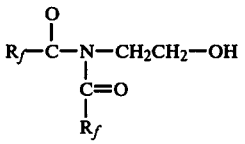  (Z = hydrogen)

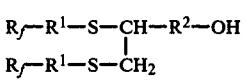

$R^9$ = methyl or hydrogen
$R^8$ is alkyl of 1 to 12 carbon atoms, or CH₂COOH or CH₂CH₂COOH.

The perfluoroalkyl alcohols and diols can also contain two $R_f$ groups as seen in the compounds illustrated below, where a is 2.

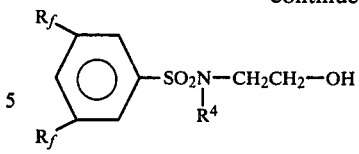

$[R_f(CH_2)_n SCH_2]_2$—CHOH     n = 1 to 12

Formula III thus also described di-$R_f$-substituted alcohols and diols. In all the above structures, $R^4$ is a branched or straight chain alkyl of 1 to 6 carbon atoms, $R^5$ is hydrogen or methyl, and $R^1$ and $R^2$ are as previously defined.

$R_f$-alcohols and diols are described in U.S, Pat. Nos. 2,803,615; 3,079,214; 3,207,730; 3,256,230; 3,332,902; 3,282,905; 3,304,198; 3,304,278; 3,361,685; 3,378,609; 3,498,946; 3,384,627; 3,384,628; 3,407,183; 3,424,285; 3,510,455; 3,547,894; 3,686,283; 3,728,151; 3,736,300; 3,759,874; 3,794,623; 3,872,858; and 3,883,596; in British Pat. Nos. 1,101,049; and 1,130,822; and in German Offenlengungsschrift No. 2,342,888.

A particularly preferred class of perfluoroalkyl substituted compounds contain the residue of an $R_f$-glycol characterized by the presence of one or two perfluoralkylthio groups on adjacent carbon atoms. The $R_f$-glycols have the structure

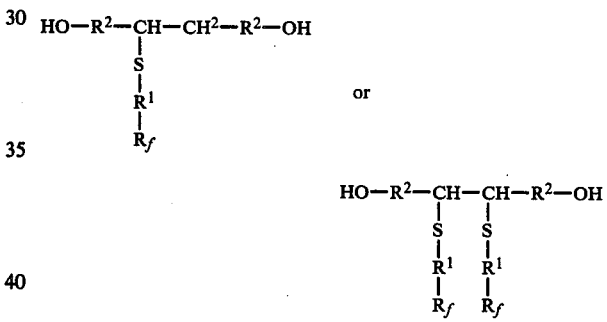

wherein $R_f$ is perfluoroalkyl of 6 to 18 carbon atoms;

$R^1$ is straight or branched chain alkylene of 1 to 4 carbon atoms;

$R^2$ is a straight or branched chain alkylene of 1 to 4 carbon atoms or $CH_2(OC_kH_{2k})_r$ wherein m is 1 to 4 k is 2 to 4 r is 1 to 20

The $R_f$-glycol can be obtained by addition of 2.0 moles of a mercaptan of formula $R_f$-$R^1$-SH to one mole of an acetylenic diol of formula HOR²-C C-R²OH or 1 mole of mercaptan to one more of a diol of the formula HOR²CH=CHR²OH wherein $R^1$, $R^2$, and $R_f$ are as described above, in the presence of an azo type free radical catalyst such as azobisisobutyronitrile at a temperature of 60° to 80° C., in bulk or in the presence of a $C_6$-$C_{10}$ alkane solvent.

A preferred class of mercaptans is disclosed in U.S. Pat. No. 3,544,663 and can be obtained by reacting a perfluoroalkyl alkyl iodide with thiourea, followed by hydrolysis.

Preferred are the compounds of this invention which contain the residue of an $R_f$-glycol, wherein $R_f$ is perfluoroalkyl of 6 to 12 carbon atoms;

$R^1$ is ethylene, $R^2$ is methylene, obtained by adding two moles 2-(perfluoroalkyl)ethyl mercaptan to one mole 2-butyn-1,4-diol or one mole of said mercaptan to one mole of 2-buten-1,4-diol.

The tetraradical rest Q (or $Q_1$) is derived from a tetracarboxylic acid or tetracarboxylic dianhydride of formula IV or a tricarboxylic acid anhydride acid chloride of formula V.

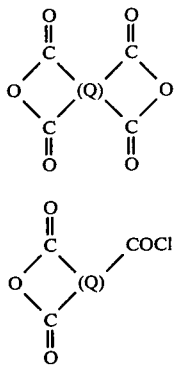

The dianhydrides of formula IV can be aliphatic, alicyclic, aromatic, or heterocyclic in general structure.

A list of suitable dianhydrides of structure IV is given below.

Generally dianhydrides of tetracarboxylic acids in which the four carboxy groups are attached in pairs to two adjacent carbon atoms have the structure of two 5-membered cyclic anhydride groups in one molecule.

1,2,4,5-benzenetetracarboxylic dianhydride
1,2,3,4-benzenetetracarboxylic dianhydride
2,3,6,7-naphthalenetetracarboxylic dianhydride
3,3',4,4'-diphenyltetracarboxylic dianhydride
1,2,5,6-naphthalenetetracarboxylic dianhydride
2,2',3,3'-diphenyltetracarboxylic dianhydride
3,3',4,4'-azobenzenetetracarboxylic dianhydride
2,3,4,5-tetrahydrofurantetracarboxylic dianhydride
2-phenyl-4,6-bis(3',4'-dicarboxyphenyl)-s-triazine dianhydride
2-diphenylamino-4,6-bis(3',4'-dicarboxyphenyl)-s-triazine dianhydride
2,2-bis-(3,4-dicarboxyphenyl)propane dianhydride
bis-(3,4-dicarboxyphenyl)sulfone dianhydride
3,4,9,10-perylenetetracarboxylic dianhydride bis(3,4-dicarboxyphenyl)ether dianhydride
1,1,2,2-ethylenetetracarboxylic dianhydride
1,2,4,5-naphthalenetetracarboxylic dianhydride
1,4,5,8-naphthalenetetracarboxylic dianhydride
decahydronaphthalene-1,4,5,8-tetracarboxylic dianhydride
4,8-dimethyl-1,2,3,5,6,7-hexahydronaphthalene-1,2,5,6-tetracarboxylic dianhydride
2,6-dichloronaphthalene-1,4,5,8-tetracarboxylic dianhydride
2,7-dichloronaphthalene-1,4,5,8-tetracarboxylic dianhydride
2,3,6,7-tetrachloronaphthalene-1,4,5,8-tetracarboxylic dianhydride
1,8,9,10-phenanthrenetetracarboxylic dianhydride
1,2,3,4-cyclopentanetetracarboxylic dianhydride
2,3,4,5-pyrrolidinetetracarboxylic dianhydride
2,3,5,6-pyrazinetetracarboxylic dianhydride
2,2-bis-(2,5-dicarboxyphenyl)propane dianhydride
1,1-bis-(2,3-dicarboxyphenyl)ethane dianhydride
bis-(2,3-dicarboxyphenyl)methane dianhydride
bis-(3,4-dicarboxyphenyl)methane dianhydride
bis-(3,4-dicarboxyphenyl)sulfone dianhydride
1,2,3,4-butanetetracarboxylic dianhydride
2,3,4,5-thiophenetetracarboxylic dianhydride
3,3'4,4'-diphenyltetracarboxylic dianhydride
3,3'4,4'-benzophenonetetracarboxylic dianahydride Other dianhydrides contemplated to be of use in this invention are synthesized by the base catalyzed addition of a dithiol to two moles of maleic anhydride or by the free radical addition of a dithiol to tetrahydrophthalic anhydride, norbornane anhydride or methylnorbornane anhydride. Such dianhydrides have the structures below:

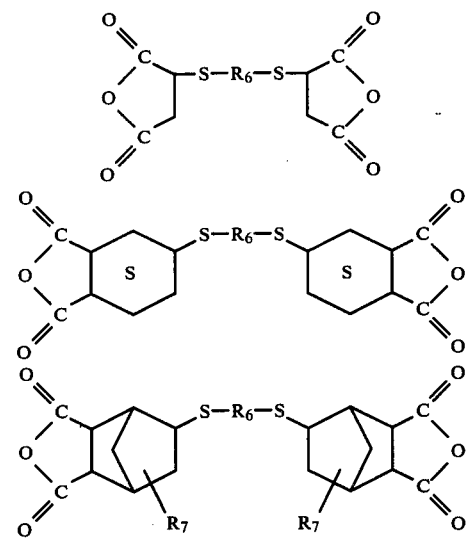

In these structures, $R_6$ is a linear or branched alkylene chain of 2 to 20 carbon atoms, which may also contain an ether oxygen or ester groups. Typical examples for $R_6$ are:

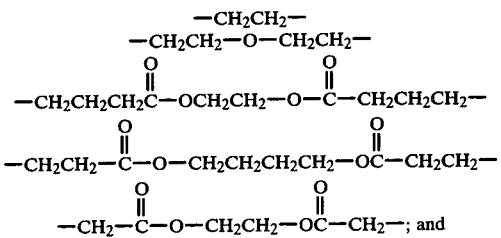

$R_7$ is hydrogen or methyl.

The anhydride acid chlorides of formula V are best exemplified by trimellitic acid anhydride acid chloride (commercially available)

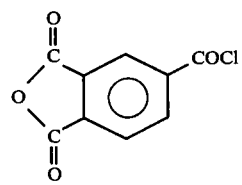

The preferred dianhydrides useful in this invention are 3,3′4,4′-benzophenonetetracarboxylic acid dianhydride, 1,2,4,5-benzenetetracarboxylic acid dianhydride,

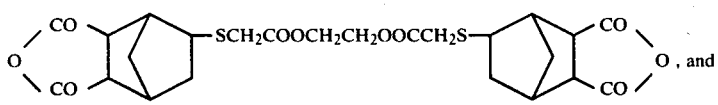

2,3,4,5tetrahydrofurantetracarboxylic acid dianhydride.

The most preferred dianhydrides are 3,3′, 4,4′-benzophenonetetracarboxylic acid dianhydride and 2,3,4,5-tetrahydrofurantetracarboxylic acid dianhydride.

The anhydrides of formula IV are generally items of commerce. They can also be prepared by conventional procedures from the corresponding acids using an acid chloride and pyridine or in the aromatic or heterocyclic series by oxidation of the corresponding tetramethyl compounds.

The compounds of this invention having structure I are prepared by reacting a mono-$R_f$ or a di-$R_f$ substituted alcohol of formula III with a dianhydride of formula IV or anhydride acid chloride of formula V in a suitable organic solvent at slightly elevated temperatures. The mol ratios of the reactants are selected so that at least one anhydride group is present in the product. This anhydride group can subsequently easily be opened up with water, alcohols or amines to give diacids, diacid salts, acidesters, and acid-amides (amicacids).

In like manner the compounds of this invention having structure I where A is group II are prepared by the same reaction described above, but using a mono-$R_f$ or a di-$R_f$ substituted diol of formula III.

The synthesis of a compound of formula I is carried out in an organic solvent which will dissolve both the $R_f$-alcohol or $R_f$-diol and the dianhydride or anhydride acid chloride at the reaction temperature. Useful solvents include ethers such as dioxane, tetrahydrofuran, ethylene glycol dimethyl ether; esters such as ethyl acetate or ethyl cellosolve acetate; amides such as N,N-dimethylformamide and N,N-dimethylacetamide, N-methylpyrrolidone; pyridine; ketones such as acetone, methyl ethyl ketone or methyl isobutyl ketone and the like. Generally any aprotic solvent or mixture of aprotic solvents which will dissolve both reactants will suffice. The reaction is carried out preferably at slightly elevated temperatures, namely between 50° and 100° C. The reaction rate is greatly influenced by the nature of the reactants, with the di-$R_f$-diols and aromatic dianhydrides reacting slower than the mono-$R_f$-diols and aliphatic anhydrides. However, in the presence of basic catalyst, such as tertiary or quaternary amines, all reactions proceed rapidly and smoothly. Preferred catalysts are quaternary ammonium compounds such as tetramethylammonium hydroxide or tetramethylammonium chloride. The product is obtained as a 10–70% solution which is a most desirable form for applications where a small amount of the compound is to be added to large volumes of resins or resin solutions.

Since these novel anhydrides are usually insoluble in resins or resin solutions unless one of the aforementioned solvents is present, the compounds of this invention usually are first reacted with the —OH or —NH groups of the resin or are otherwise transformed into a soluble or compatible state. For incorporation into polyurethane foams, for instance, the anhydride or dianhydride is first reacted with part of the polyol component, as described in Example 22 before mixing it into the final formulation; for incorporation into aqueous resin solutions, the compounds are reacted with water solubilizing alcohols or amines such as polyethylene oxide, bis-amino propyl ether of polyethylene oxide, or N,N-dialkylaminealcohols, or N,N-dialkylaminoalkyl diamines. Preferred reactants are N,N-dimethylaminoethanol and N,N-dimethylaminopropane-1,3-diamine. This reaction leads to formation of amphoteric groups and easy water dispersibility at high and low pH. If only solubility in basic medium is required the dicarboxylate derivative of the anhydride is sufficient, for instance the ammonium salt.

Since the water soluble forms of the novel compounds are not especially good surface-active agents for water, or the water-resin solutions as such, it is often useful to add another surfactant to aqueous systems, one which is especially designed to reduce the surface tension of water. In this way good wetting of the aqueous phase is initially achieved whereafter the polyfunctional $R_f$-compounds of this invention become effective after the water has been evaporated. Especially useful cosurfactants for water-based coatings are ionic, cationic and amphoteric, $R_f$-surfactants, which will reduce the surface tension of water to below 20 dynes/cm.

Thus, combination of the novel compounds of this invention with conventional, ionic $R_f$-surfactants for use in aqueous resin systems is another embodiment of this invention. The unique usefulness of these novel compounds is demonstrated in detail in the examples.

Thus, the compounds of this invention are useful in the development of a "dual wetting" system for water based coatings for hard-to-wet surfaces. Such a system comprises two parts. One is based on a perfluoroalkyl ($R_f$) ionic surfactant, effective in reducing the surface tension of the water phase, and the second part derived from the perfluoroalkyl dianhydrides of this invention, effective in the resin phase. Use of this dual system can provide complete (100%) coverage of hard-to-wet substrates, for instance industrial grade electrolytic tin plate when coated by an aqueous epoxy resin coating system.

It is understood that the scope of the invention is not limited by the following postulations nor that the effectiveness of the dianhydrides of this invention necessarily results from the proposed explanations thereof. The following postulations appear to offer a plausible mechanism by which the "dual wetting" system may operate in order to effect its efficacious activity during the coating of aqueous based resin systems on hard-to-wet surfaces.

When a polymeric thermosetting resin coating, such as a water based epoxy resin, is applied to a hard-to-wet substrate, the following stages appear to occur:

1. The surface is first wetted by the aqueous phase of the coating system. A surfactant which can reduce the interfacial tension between the water and the substrate will be beneficial. Ionic perfluoroalkyl compounds are particularly useful in this stage.

2. As the applied coating system is then heated, the water present evaporates. The resin component viscosity will be initially low, dependent on temperature and cure rate, and as the water evaporates, the surface tension of the resin phase itself will determine wetting. If it is high, the resin may then retract from the surface, bead up and cause an imperfect coating of the substrate to occur.

This state of affairs can be avoided if the surfactant effective in the aqueous phase has also sufficient compatibility within the resin to be effective in preventing the undesirable beading up of the resin. Generally, ionic type surfactants are poorly compatible with resins, while non-ionic types, which are more compatible, are not as good surfactants for the water phase.

However, the presence of a second surfactant compound tailored for optimum compatibility in the resin phase will overcome the problem of beading up and poor surface wetting noted above. This second surfactant causes the surface tension of the resin phase to remain low, prevents bead up of the resin and assures complete coverage of the substrate with the resin. This will allow the resin to cover the surface as completely in the absence of water as did the original aqueous resin solution.

3. Continued heating effects complete resin cure with complete coverage of the substrate surface by the cured resin.

The "dual wetting" system of this invention provides for (a) the best surfactant available for the initial wetting out the aqueous resin coating system; and (b) the best surfactant available for the subsequent reducing of the surface tension of the resin phase during the critical precuring step as the water is evaporated from the applied aqueous coating system.

The advantages of the instant invention are thus that optimal performance is achieved throughout the entire coating operation and a greater range of aqueous resin coating systems can be successfully used.

In the "dual wetting" system the surfactant to be effective in the aqueous phase can be the ionic type surfactants normally incompatible in most resins. The second surfactant of the dual system is preferably a multifunctional compound, such as the dianhydrides of this invention, capable of coreacting with the curable resin, thus preventing any loss of surfactant by bleedout.

Attempts to use one surfactant active in both the aqueous and the resin phases where a water soluble structure provides some compatibility of the surfactant in the resin is exemplified in the prior art as seen with commercial products which are $R_f$ non-ionic surfactants. This approach represents a compromise and a significant loss in coverage of the substrate occurs during the curing step.

In the instant invention, an effective $R_f$-amphoteric, anionic or cationic surfactant is combined with an $R_f$-dianhydride compound or its derivatives of this invention.

A preferred surfactant combination consists of an $R_f$-amphoteric surfactant

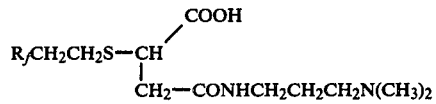

Lodyne S-100, (as described in Ser. No. 538,432, incorporated herein by reference), which is effective in the aqueous phase of the water-based resin coating system, with a reactive water soluble derivative of an $R_f$-dianhydride as described earlier in this application. The effectiveness of the use of any one surfactant on effecting coverage of an industrial grade electrolytic tin substrate, wet or after cure, is seen on Table A. Only the $R_f$-amphoteric surfactant Lodyne S-100 gave 100 % wet coverage, but after cure only 45% coverage remained. With other commercial products such as FC-430 or even the derivative of an instant dianhydride (Example 14a) when used alone, a compromise in coverage was attained, but none achieved the desired and necessary 100% coverage both wet and after cure. However, the instant derivative of (Example 14a) was able to prevent shrinkage of the initially wetted substrate coating during cure.

It is noted on Table A from the surface tension measurements of the water solutions shown that the critical property which determines wetting of a surface is not surface tension per se, but more likely interfacial tension.

Table A

Aqueous Epoxy (of Ex. 17): Wetting of Electrolytic Tin using Various Additives
(#7 wire rod; 200° C./10 min)

| Sample No. | Additive Type | % in solids | % F | $\gamma_s$ [dyne/cm] | % Coverage of Tin | |
|---|---|---|---|---|---|---|
| | | | | | wet | after cure |
| 1 | Pluronic L-72 (polyox derivative)[1] | 0.5 | — | | 80 | 50 |
| 2 | Pluronic L-72 (polyox derivative)[1] | 1.0 | — | 35.8 | 80 | 50 |
| 3 | BYK 301 (silicone)[2] | 0.5 | — | | 70 | 60 |
| 4 | BYK 301 (silicone)[2] | 1.0 | — | 33.4 | 85 | 75 |
| 5 | FC-430 ($R_f$-surfactant nonionic)[3] | 0.5 | 0.067 | | 75 | 65 |
| 6 | FC-430 ($R_f$-surfactant nonionic)[3] | 1.0 | 0.134 | 20.7 | 75 | 60 |
| 7 | Example 14a ($R_f$-dianhydride) derivative | 0.18 | 0.067 | | 65 | 65 |
| 8 | Example 14a ($R_f$-dianhydride) derivative | 0.36 | 0.134 | 33.8 | 85 | 85 |
| 9 | Lodyne S-100 ($R_f$-surfactant amphoteric)[4] | 0.15 | 0.067 | 17.1 | 100 | 45 |
| 10 | Control | — | — | 40.1 | 50 | 30 |

1. BASF Wyandotte
2. Mallinckrodt
3. 3M Company
4. CIBA GEIGY

The effectiveness of the "dual surfactant" system of the present invention is explicitly illustrated on Table B. Clearly the $R_f$-amphoteric surfactant Lodyne S-100 is most effective in giving essentially 100% wet coverage regardless of what second surfactant was present in the system. None of the second surfactants tested, including FC-430, an $R_f$ non-ionic type, were effective in giving after cure coverage of the tin substrate save Example 14a the derivative of the instant $R_f$ dianhydride of Example 1b, where excellent coverage (up to 100%) depending on the specific ratios of surfactants used after cure was attained. The combination of both Lodyne S-100B and Example 14a was the only dual surfactant system to prevent shrinkage (bead up) of the initially (100%) wetted substrate coating during cure as seen on Table B. The compounds of this invention can, of course, be combined with other $R_f$ ionic (amphoteric, cationic and anionic) surfactants to achieve the above described effect.

they are used in polyurethane chemistry; polyamines used as epoxy curing agents; siloxane diols; isocyanate terminated prepolymers; methylolated resins, such as methylolated melamines and ureas; hydroxy terminated polybutadienes; other hydroxy bearing polymers, such as hydroxy ethyl cellulose, hydroxy alkyl acrylates - and methacrylates polymers and copolymers and polyvinyl alcohol.

Thus the novel $R_f$-anhydrides of this invention are the precursors for a large group of resin-compatible wetting agents. Derivatives produced from them impart excellent wetting abilities to polycondensate resing systems. In many cases, they act as adhesion promoters.

Experimentally these compounds have been found to

Table B

Aqueous Epoxy (of Ex. 17): Wetting of Electrolytic Tin using Additive Combination #7 wire rod; 200° C./10 min)

| Sample No. | Lodyne S-100 $R_f$ surfactant % by Wt. | Other Surfactant | % by Wt. | % F (solids)[1] s | r | % Coverage of Tin wet | after cure |
|---|---|---|---|---|---|---|---|
| 1 | 0.15 | PL-72 (Pluronic)[2] | 0.5 | 0.067 | — | 100 | 10 |
| 2 | 0.07 | BYK 301 (Silicone)[3] | 0.25 | 0.038 | — | 90 | 60 |
| 3 | 0.15 | BYK 301 | 0.5 | 0.067 | — | 100 | 10 |
| 4 | 0.07 | FC-430 ($R_f$ type)[4] | 0.25 | 0.134 | — | 95 | 65 |
| 5 | 0.15 | FC-430 | 0.5 | 0.268 | — | 98+ | 15 |
| 6 | 0.047 | Example 14a | 0.12 | 0.022 | 0.044 | 80 | 80 |
| 7 | 0.07 | Example 14a | 0.09 | 0.033 | 0.033 | 95 | 95 |
| 8 | 0.105 | Example 14a | 0.046 | 0.050 | 0.017 | 90 | 40 |
| 9 | 0.15 | Example 14a | 0.18 | 0.067 | 0.067 | 100 | 100 |

[1]surfactant type: s reactant type: r
[2]BASF Wyandotte
[3]Mallinckrodt
[4]3M Company One example of a particularly preferred $R_f$ dianhydride of this invention is the compound of Example 1.

improve adhesion of a thermoset acrylic resin to aluminum (from failing to passing a cross-cut adhesion test),

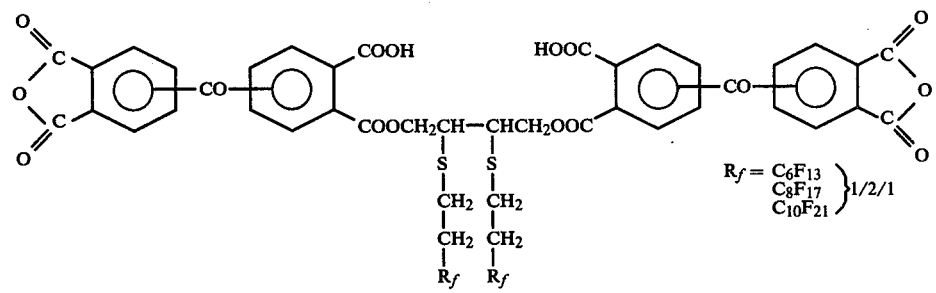

Although the anhydrides and dianhydrides of this invention are insoluble in polyhydric resins, such as polyols or polyamines, they can be solubilized by ring opening reaction with these compounds. For instance, in order to incorporate the novel $R_f$-moieties into a polypropylene oxide diol, 5 g of a 33% solution of the new $R_f$-anhydride compound are heated with 5–20 g of the polyol until a clear product is obtained; the solvent can be evaporated and the remaining $R_f$-modified resin, which contains 1–10% fluorine, can be further diluted with unmodified resin to the desired fluorine level usually between 0.001% and 0.5%.

Many reactive polymers or prepolymers can be treated and modified with this method: polyethylene oxide diols, polypropylene oxide diols, bis-2-aminopropyl ethers of polyalkylene oxides, poly-n-butylene oxide diols; polyester diols from dibasic acids and diols, as and of a polysulfide sealant to concrete.

In certain other cases, dependent on polymer and substrate, they can also act as mold release agents.

These water-soluble derivatives are compounds of high reactivity and of unique structure. During the curing process they co-react with the resin. Thus, they are prevented from bleeding out, and a low surface tension, that is good wetting, is maintained throughout the cure cycle.

A particularly preferred derivative of the dianhydride of Example 1 illustrated above is prepared by reaction of one mole of the dianhydride with two moles of an N,N-substituted aminoalcohol or diamine such as N,N-dimethylethanolamine or N,N-dimethylpropane-1,3-diamine. One such derivative has the structure below:

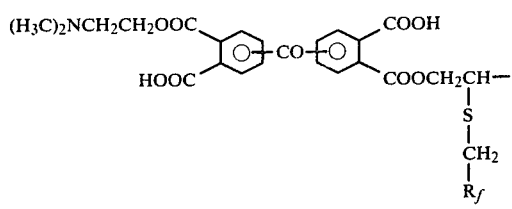
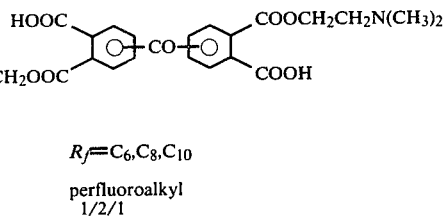

$R_f = C_6, C_8, C_{10}$ perfluoroalkyl
1/2/1

This derivative of an $(R_f)_2$-dianhydride is especially designed for incorporation into aqueous and highly polar resin systems.

It is soluble or dispersible in aqueous or polar organic resin solutions, as well as in resins themselves. However, its solubility sometimes is limited to low molecular weight and polar components of resin systems (amine-hardeners; alkyd resins; low molecular weight polyols; methendic anhydride). If it is used with water-based coatings, such as aqueous epoxies, it is preferably used in combination with an ionic $R_f$-surfactant designed to reduce the surface tension of water.

Dependent on resin systems and substrates, the compounds of this invention behave either as mold release agents or as adhesion promoters.

a. With a thermosetting acrylic resin, the anhydrides of this invention acted as adhesion promoters for coatings of such resins on aluminum substrates.

b. With polysulfide sealants, the dianhydrides of this invention perform as internal mold release agents when the substrates were smooth surfaces such as glass or aluminum, but acted as excellent adhesion promoters when the polysulfide sealant was bonded to a "rough" concrete surface.

The $R_f$-anhydrides of this invention also possess valuable utility as a control agent in the perparation of polyurethane foams which have lower densities and a larger plurality of very small uniform bubbles than in normal polyurethane foams. These $R_f$-dianhydrides also act as mold release agents with the polyurethane foams, The preparation and unique usefulness of the novel compounds of this invention are demonstrated in detail in the following examples. The examples are meant to illustrate the invention without introducing any limitation thereof whatsoever.

In the following examples, $R_f$ refers to a mixture of perfluoroalkyl groups in the following weight ratio unless otherwise indicated:

$C_6F_{13}/C_8F_{17}/C_{10}F_{21}$ = essentially 1/2/1 but may also contain a small quantity of $C_{12}F_{25}$.

Examples 1 to 9 illustrate the preparation of synthesis of compounds of this invention.

It must be pointed out that the amounts of the compounds of this invention necessary to achieve the aforementioned effects such as surfactant, mold release, adhesion promotion, polyurethane foam control, etc., in a system will vary from 0.003 to 2.0% by weight of said compounds to give a fluorine concentration in the polymer system of 0.001 to 0.5% fluorine.

It must be further pointed out that the perfluoroalkyl substituted anhydrides of this invention are normally prepared as a mixture of formula isomers. While the pure isomers can be separated by standard organic laboratory techniques such as chromatography, vacuum distillation, selective fractionation and the like, it is quite unnecessary and not economic to do so since the valuable surface tension properties of these materials reside essentially equally with all formula isomers.

The mixture of formula isomers is caused by the asymmetry of most of the starting intermediates which are reacted with the $R_f$ alcohol or diol usually through the opening of an anhydride five-membered ring. This reaction of the alcohol or diol with the anhydride can result in a carboxyl group on one carbon atom and an ester group on an adjacent carbon atom, but there is no particular selection as to which carbon atom will bear which group. If the overall molecule were otherwise symmetrical, it would result in one isomer. However, in most of the instant cases, mixtures of isomers are obtained.

When in Example 1, one mole of the $R_f$ diol (A) reacts with two moles of benzophenone-3,3',4,4'-tetracarboxylic acid dianhydride (BTDA) a mixture of three formula isomers are formed.

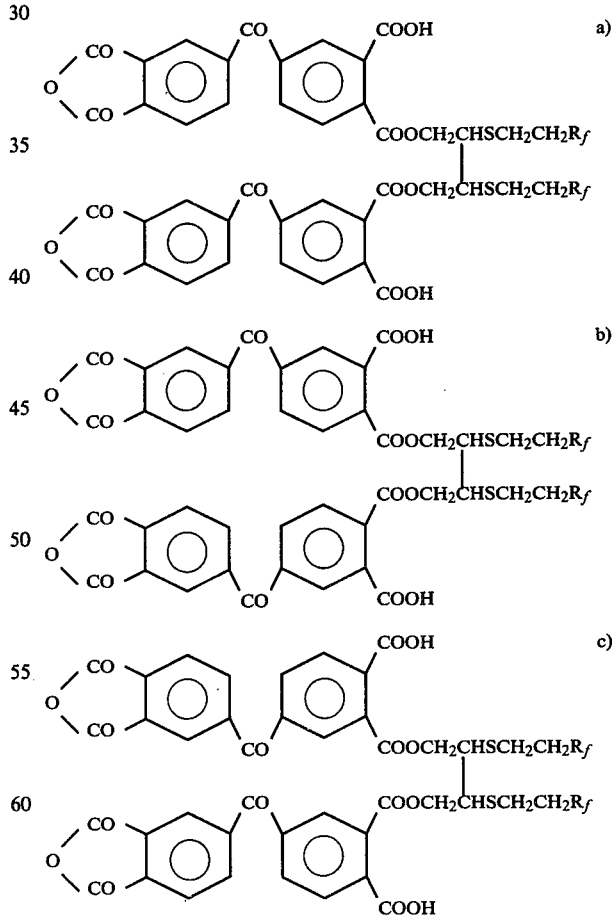

These three structures may be combined into one structure which definitively describes the mixture of the three formula isomers above as seen below:

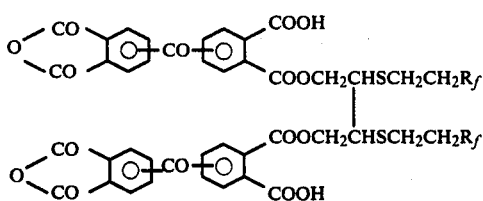

In like manner, when the anhydride groups at the left of the above structure are opened as seen in Example 14 with N,N-dimethylaminoethanol or a like tertiary amine containing compound a plurality of additional formula isomers are possible as the remaining anhydride groups are opened. The structure below where the exact position of the center carbonyl group —CO— is floating between the two sets of adjacent carbon atoms properly describes such mixtures of formula isomers produced.

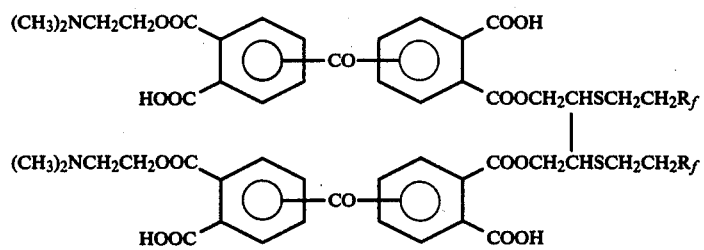

Again there is no need to separate the various isomers which are all water-soluble or water-dispersible as seen in Example 14.

EXAMPLE 1

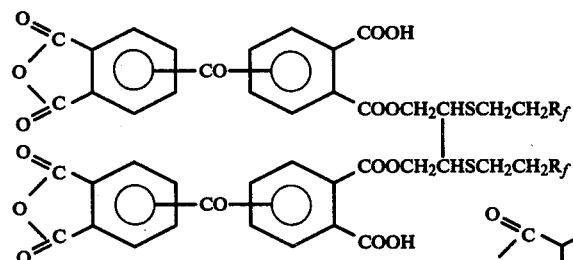

(a) An $(R_f)_2$-diol of structure A $$C_8F_{17}-CH_2CH_2-S-CH-CH_2OH$$
$$|$$
$$C_8F_{17}-CH_2CH_2-S-CH-CH_2OH$$

(A)

20.44 g (0.02 mole) and 67 g glyme (ethylene glycol dimethyl ether) were heated to 60° C. under nitrogen. 3,3',4,4'-benzophenonetetracarboxylic acid dianhydride (BTDA), 14.17 g (0.044 mole) and 0.4 g triethylamine were added and the reaction mixture stirred at 60° C. for 10 hours, at which time IR analysis indicated completeness of the reaction.

The solution was filtered to remove unreacted BTDA and the residue was evaporated to dryness on rotary evaporator. The resulting brittle solid was ground and dried under high vacuum for 8 hours. 33.2 g of a light tan powder (99.8 % yield) was obtained. MP: 127–133° C.

| Analytical Data | Calculated | Found |
|---|---|---|
| anhydride equiv. wt. | 833 | 855 |
| acid equiv. wt. | 833 | 730 |
| fluorine, % | 39.0 | 39.4 |

(b) A dianhydride of the same formula structure as in Example 1a was also be prepared using an $(R_f)_2$-diol of structure A

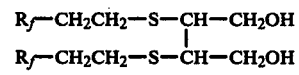

$$R_f-CH_2CH_2-S-CH-CH_2OH$$
$$|$$
$$R_f-CH_2CH_2-S-CH-CH_2OH$$

where $R_f$ refers to a mixture of perfluoroalkyl groups in the following weight ratio:

$C_6F_{13}/C_8F_{17}/C_{10}F_{21}$ = essentially 1/2/1.

The product is a light tan powder having a m.p. of 110°–116° C.

EXAMPLE 2

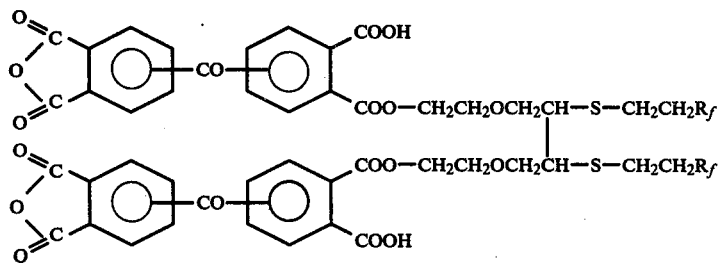

Following the same procedure as in Example 1, an $(R_f)_2$-diol of structure B $$R_f-CH_2CH_2-S-CH-CH_2OCH_2CH_2OH$$
$$|$$
$$R_f-CH_2CH_2-S-CH-CH_2OCH_2CH_2OH$$

(B), 21 g (0.02 mole) was reacted with 14.17 g (0.044 mole) BTDA. 33.5 g of a light tan powder was obtained representing 98% yield. MP: 105°–108° C.

| Analytical Data | Calculated | Found |
|---|---|---|
| anhydride equiv. wt. | 800 | 741 |
| fluorine, % | 32.9 | 31.9 |

EXAMPLE 3

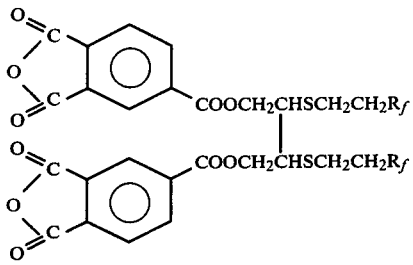

Trimellitic anhydride acid chloride 33.7 g (0.160 mole) was dissolved in 200 ml dry "glyme" (ethylene glycol dimethyl ether) and placed in an addition funnel on top of a 500 ml 3-necked flask equipped with stirrer, nitrogen-inlet and drying tube. In the flask 77.77 g (0.075 mole) (R$_f$)$_2$-diol of structure (A) (Example 1) and 12.65 g (0.160 mole) pyridine were dissolved in 100 ml dry "glyme". The solution was stirred at room temperature under nitrogen while the anhydride/acid chloride solution was added over 45 minutes. A white precipitate formed and the exothermic reaction raised the temperature of the mixture to 34° C. After stirring another 15 minutes hydrochloride was filtered off and the glyme solution evaporated to near dryness. The residue was stirred with 500 ml anhydrous ethyl ether, filtered and evaporated to dryness. 82.4 g of a brittle material was collected (79.3% yield). MP: 66°-72° C.

| Analytical Data | Calculated | Found |
|---|---|---|
| anhydride equiv. wt. | 685 | 746 |
| fluorine, % | 46.0 | 47.6 |

EXAMPLE 4

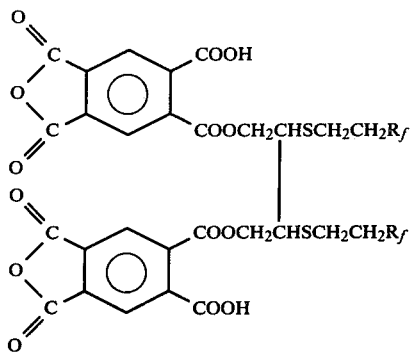

Following the procedure of Example 1, 20.44 g (0.02 mole) of (R$_f$)$_2$-diol of structure (A) and 8.72 g (0.040 mole) 1,2,4,5-benzenetetracarboxylic acid dianhydride (pyromellitic dianhydride) were reacted in the presence of 0.05 g. tetramethylammonium chloride. After filtration and drying, a brittle tan powder was obtained in 96% yield; MP: 97°-115° C.

| Analytical Data | Calculated | Found |
|---|---|---|
| anhydride equiv. wt. | 588 | 610 |
| fluorine % | 40.5 | 42.1 |

EXAMPLE 5

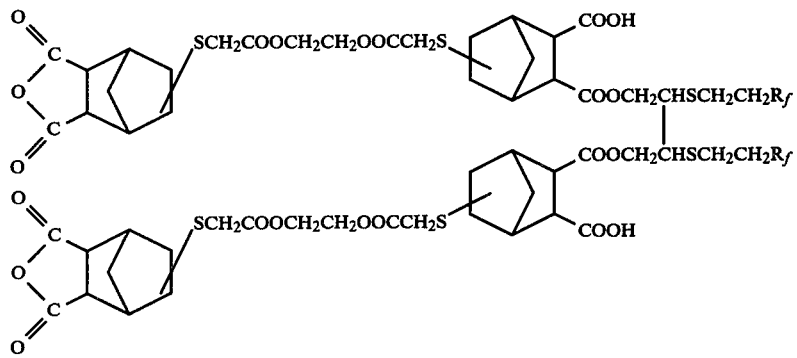

Following the procedure of Example 1, 20.44 g (0.02 mole) of (R$_f$)$_2$-diol of structure (A) and 22.64 g (0.040 mole) of the dianhydride obtained by free-radical addition of 1 mole of ethylene bis-mercaptoacetate to 2 moles of 5-norbornene-2,3-dicarboxylic acid anhydride (nadic anhydride) were reacted in the presence of 0.4 g triethylamine. After filtration and drying, the product was obtained as a light yellow powder in 94% yield. MP: 65°-70° C.

| Analytical Data | Calculated | Found |
|---|---|---|
| anhydride equiv. wt. | 1053 | 1111 |
| fluorine, % | 27.3 | 28.6 |

EXAMPLE 6

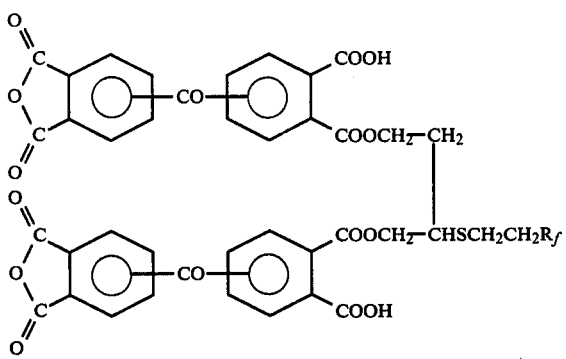

(a) Using the procedure of Example 1, 5.68 g (0.01 mole) of the diol of structure C

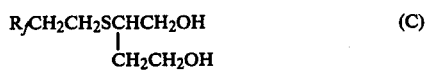

and 6.44 g (0.02 mole) of 3,3′,4,4′-benzophenonetetracarboxylic acid dianhydride (BTDA) were heated in the presence of 0.4 g of triethylamine. After removal of the solvent, the product was obtained as a brittle yellowish solid; MP: 116°–121° C. in 95% yield.

| Analytical Data | Calculated | Found |
| --- | --- | --- |
| anhydride equiv. wt. | 606 | 595 |
| fluorine, % | 26.6 | 23.3 |

(b) A dianhydride of the same formula structure as shown above may also be prepared using the $R_f$-diol of the structure

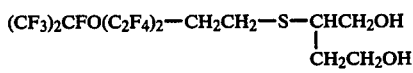

using the procedure described above.

EXAMPLE 7

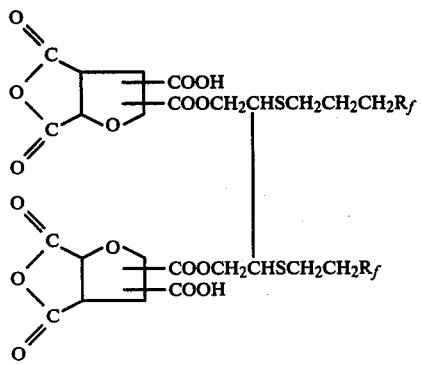

Following the procedure of Example 1, 20.44 g (0.02 mole) of $(R_f)_2$-diol of structure (A) and 8.48 g (0.04 mole) of 2,3,4,5-tetrahydrofurantetracarboxylic acid dianhydride were heated in the presence of 0.044 g of tetramethylammonium chloride. After removal of solvent, the product was obtained as a brown solid in 98% yield. MP: 155°–160° C.

| Analytical Data | Calculated | Found |
| --- | --- | --- |
| anhydride equiv. wt. | 763 | 833 |
| fluorine, % | 42.4 | 40.5 |

EXAMPLE 8

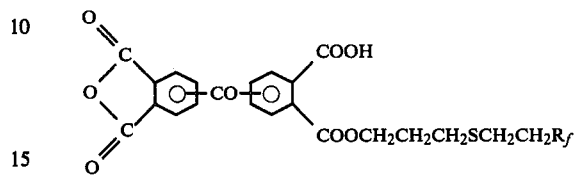

Using the procedure of Example 1, 10.75 g (0.02 mole) of 6-perfluoroalkyl-4-thiahexane-1-ol and 6.44 g (0.02 mole) of BTDA were heated in the presence of 0.022 g of tetramethylammonium chloride. The solvent was removed on a rotary evaporator leaving a yellowish brittle solid. MP: 123°–132° C.

| Analytical Data | Calculated | Found |
| --- | --- | --- |
| anhydride equiv. wt. | 860 | 1026 |
| fluorine, % | 37.6 | 35.3 |

EXAMPLE 9

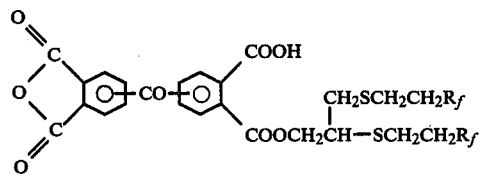

Following the procedure of Example 1, 15.24 g (0.015 mole) of 2,3-di-(1,1,2,2-tetrahydroperfluoroalkylthio)-propanol-1 and 4.83 g (0.015 mole) of BTDA were heated in the presence of 0.20 g of triethylamine. The solvent was stripped off on a rotary evaporator leaving a yellowish brittle solid. MP: 80°–90° C., in 95% yield.

| Analytical Data | Calculated | Found |
| --- | --- | --- |
| anhydride equiv. wt. | 1338 | 1307 |
| fluorine, % | 48.3 | 47.0 |

EXAMPLE 10

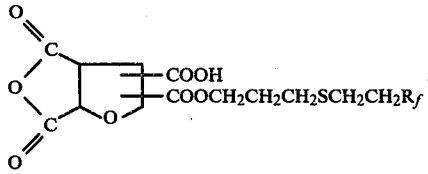

Following the procedure of Example 1, 10.76 g (0.02 mole) of 6-perfluoroalkyl-4-thiahexane-1-ol and 4.24 g (0.02 mole) of tetrahydrofuran-2,3,4,5-tetracarboxylic acid dianhydride were heated in the presence of 0.02 g of tetramethyl ammonium chloride. After removal of solvent, the product was obtained as a tan glass-like solid, m.p. 150°–160° C.

| Analytical Data | Calculated | Found |
|---|---|---|
| anhydride equiv. wt. | 750 | 889 |
| fluorine, % | 43.1 | 40.0 |

EXAMPLE 11

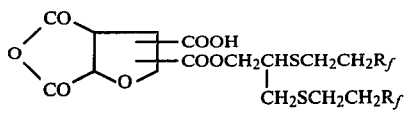

Following the procedure of Example 1, 15.24 g (0.015 mole) of 2,3-di(1,1,2,2-tetrahydroperfluoroalkylthio)-propane-1-ol and 3.18 g (0.015 mole) of tetrahydrofuran-2,3,4,5-tetracarboxylic acid dianhydride were heated in the presence of 0.02 g of tetramethyl ammonium chloride. After removal of solvent, the product was obtained as a tan glass-like solid.

| Analytical Data | Calculated | Found |
|---|---|---|
| anhydride equiv. wt. | 1228 | 1042 |
| fluorine, % | 52.6 | 51.47 |

EXAMPLE 12

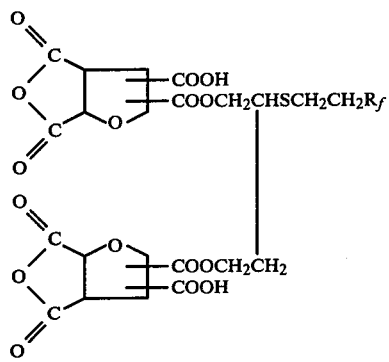

Following the procedure of Example 1, 8.52 g (0.015 mole) of 2-(1,1,2,2-tetrahydroperfluoroalkylthio)-butane-1,4-diol and 6.36 g (0.03 mole) of tetrahydrofuran-2,3,4,5-tetracarboxylic acid dianhydride were heated in the presence of 0.033 g of tetramethylammonium chloride. After removal of solvent, the product was obtained as a tan brittle solid, m.p. 123°–126° C.

| Analytical Data | Calculated | Found |
|---|---|---|
| anhydride equiv. wt. | 496 | 623 |
| fluorine, % | 32.5 | 31.07 |

EXAMPLE 12a

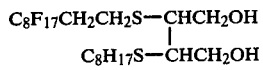

4.30 g (0.050 mole) of 2-butyne-1,4diol, 7.32 g (0.050 mole) of octyl mercaptan, 24.03 g (0.050 mole) of 1,1,2,2-tetrahydroperfluorodecylmercaptan and 1.64 g (0.010 mole) of azobisisobutyronitrile were mixed together and sealed, under nitrogen, in an ampol. The reactants were heated at 75° C. for 20 hours in a shaker bath. On cooling, a soft semisolid was obtained, which by GC analysis was observed to be a mixture of 3 products,

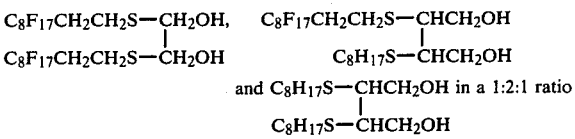

and $C_8H_{17}S-CHCH_2OH$ in a 1:2:1 ratio
    |
    $C_8H_{17}S-CHCH_2OH$

EXAMPLE 12b

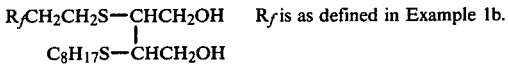   $R_f$ is as defined in Example 1b.

4.30 g (0.050 mole) of 2-butyne-1,4-diol, 7.32 g (0.050 mole) of octylmercaptan, 23.52 g (0.050 mole) of 1,1,2,2-tetrahydroperfluoroalkylmercaptan and 1.64 g (0.010 mole) of azobisisobutyronitrile were sealed, under nitrogen, in 75° C. for 16 hours in a shaker bath. On cooling, the product was obtained as a soft semisolid, bearing the same distribution of diols as in Example 12a.

| Analytical Data | Theory | Found |
|---|---|---|
| % Fluorine | 43.97 | 42.5 |
| Equivalent wt., OH | 702 | 768 |

EXAMPLE 13

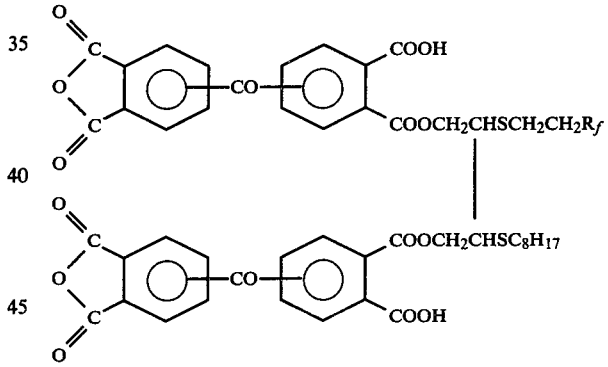

Following the procedure of Example 1, 7.78 g (0.01 mole) of the diol mixture prepared in Example 12b and 6.44 g (0.02 mole) of benzophenone-3,3',4,4'-tetracarboxylic acid dianhydride were heated in the presence of 0.040 of triethylamine. After evaporation of the solvent, the product was obtained as a yellow waxy solid, containing 50% of the above compound.

| Analytical Data | Calculated | Found |
|---|---|---|
| anhydride equiv. wt. | 706 | 766 |
| flourine, % | 23.9 | 22.5 |

EXAMPLE 14

(a) 10 g of the compound of Example 1b were disolved in 20 g N,N-dimethylformamide and heated to 80° C. for 20 minutes with 1.5 g, or three times the molar amount of N,N-dimethylaminoethanol. A water soluble product was obtained which has the following structure:

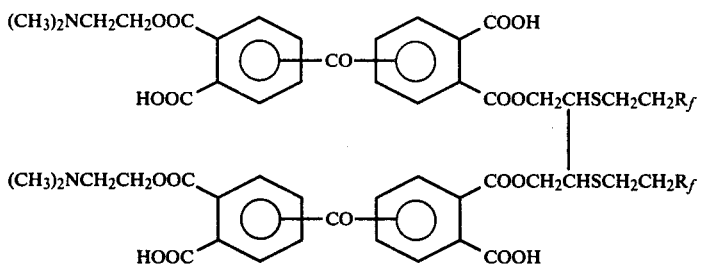

Using the same procedure as in Example 14a, the anhydrides of Examples 6–12 were also reacted with N,N-dimethylaminoethanol to give water soluble products having the corresponding structures.

| Reaction Product of N,N-dimethylaminoethanol and R$_f$-anhydride example number | Sample Number R$_f$-Anhydride |
|---|---|
| 14b | 6a |
| 14c | 7 |
| 14d | 8 |
| 14e | 9 |
| 14f | 10 |
| 14g | 11 |
| 14h | 12 |
| 14i | 13 |

EXAMPLE 15

Following the procedure of Example 14, the compound of Example 1b was reacted with three times the molar amount of the following compounds: N,N-dimethyl-propane-1,3-diamine; N-methyl-diethanolamine; N-methyl-di-(3-aminopropyl)-amine; 1,4-bis(3-aminopropyl)piperazine; N,N-diethylpropane-1,3-diamine; N-dimethylamino-2-propanol; N-dimethylamino-1-propanol; N,N,N'-trimethyl-1,2-ethylenediamine; N,N-bis[2-hydroxypropyl]aniline; N-(3-aminopropyl)-morpholine. In all cases water-soluble half ester or half amide products were obtained. These stayed dissolved in water under both basic and acidic conditions.

The compounds of Example 2–13 could also be reacted with N,N-dimethylaminoethanol or with any of the above listed compounds to give the corresponding water-soluble half ester or half amide products.

EXAMPLE 16

5g of samples of the di-anhydride of Example 1 (33% in glyme) were mixed with 20 g of the following compounds:
polyethylene oxide diol of MW: 600
polyethylene oxide diol of MW: 2000
polypropylene oxide diol of MW: 1010
polytetramethylene diol oxide of MW: 1000
bis-(2-aminopropyl) ether of polyethylene oxide of MW: 600 Jeffamine ED (Jefferson Chemical Co.)
bis-(2-aminopropyl) ether of polyethylene oxide of MW: 900 Jeffamine ED (Jefferson Chemical CO.)
bis-(2-aminopropyl) ether of polypropylene oxide of MW: 400 Jeffamine D (Jefferson Chemical Co.)
bis-(2-aminopropyl) ether of polypropylene oxide of MW: 1000 Jeffamine D (Jefferson Chemical Co.)
bis-(2-aminopropyl) ether of polypropylene oxide of MW: 2000 polyester diol from adipic acid and diethylene glycol of MW: 1000 (Fomrez F18-62; Witco Chemical Co.)

The samples were slowly heated to 90° C. until all glyme had evaporated, then heated to 150° C. for 2 hours; they formed clear, homogeneous solutions which could be further diluted with the original unmodified resin.

These resins modified by the R$_f$-dianhydride can be used in a myriad of applications where surface tension modification is an important consideration. The following examples show the usefulness of the novel compounds.

EXAMPLE 17

A water based coating formulation was mixed together, consisting of 28.6 parts of water soluble, crosslinkable resin, containing polyethylene oxide segments as water solubilizing units and being derived from diepoxides, 15.4 parts of a crosslinking melamine resin (Uformite, MM-83 from American Cyanamid) and 56 parts water. This aqueous resin was applied with a No. 6 wound wire rod to electrolytic tin plate, which has a remaining layer of a hydrocarbon-type oily impurity from processing and is especially difficult to wet. The samples were cured in a circulating air oven at 200° C. for 10 minutes.

Surface active compounds were incorporated into the formulation to improve wetting, which was judged visually and expressed in percent covered surface area. The results are tabulated below.

| Ex 17 | Additive, Chemical Type | % of Solids | % F | Coverage % before cure | Coverage % after cure | Difference |
|---|---|---|---|---|---|---|
| a | Pluronic L-72 (Wyandotte Chem Co) nonionic hydrocarbon | 0.5 | — | 80 | 50 | −30 |
| aa |  | 1.0 | — | 80 | 50 | −30 |
| b | BYK-301 (Mallinkrodt Co) silicone type | 0.5 | — | 70 | 60 | −10 |
| bb |  | 1.0 | — | 85 | 75 | −10 |
| c | FC-430 3M Company) nonionic fluorinated | 0.5 | 0.067 | 75 | 65 | −10 |
| cc |  | 1.0 | 0.134 | 75 | 60 | −15 |
| d | LODYNE ® S-100 (CIBA-GEIGY) amphoteric fluorinated | 0.15 | 0.067 | 100 | 45 | −55 |
| e | Compound of Example 14a | 0.18 | 0.067 | 65 | 65 | 0 |
| ee | Compound of Example 14a | 0.36 | 0.134 | 85 | 85 | 0 |
| f | None | — | — | 50 | 30 | −20 |
| g | Compound of Example 14b | 0.2 | 0.05 | 80 | 77 | −3 |

Only the novel compounds of this invention (e,ee, g) essentially prevent a reduction of covered surface area during curing; only the ionic fluorinated compound of Example (d) gives a 100% wetting of the substrate by the aqueous phase.

EXAMPLE 18

The water based coating formulation of Example 17 was applied with different additives in combination with the amphoteric fluorinated surfactant LODYNE ® S-100. Application and evaluation was done as in Example 17.

| Ex 18 | LODYNE® S-1000 % | Other Additive | % of Solids | Coverage % before cure | Coverage % after cure | Difference |
|---|---|---|---|---|---|---|
| a | 0.15 | Pluronic L-72 | 0.5 | 100 | 10 | −90 |
| b | 0.15 | BYK-301 | 0.5 | 100 | 10 | −90 |
| c | 0.15 | FC-430 | 0.5 | 100 | 15 | −85 |
| d | 0.15 | Compd of Ex 14a | 0.18 | 100 | 100 | 0 |
| e | 0.10 | Compd of Ex 14a | 0.05 | 90 | 40 | −50 |
| f | 0.07 | Compd of Ex 14a | 0.09 | 95 | 95 | 0 |
| g | 0.05 | Compd of Ex 14a | 0.12 | 80 | 80 | 0 |
| h | 0.10 | Compd of Ex 14b | 0.10 | 100 | 100 | 0 |

Using the novel compounds of Examples 14a and 14b at a level above 0.05% (of solids) the original good coverage of the substrate resulting from the use of amphoteric LODYNE ® S-100 is retained during the curing step.

EXAMPLE 19

To an aqueous can coating formulation of an epoxy resin modified with polyethylene oxide to form a water emulsifiable adduct (70 grams) and an aminoplast melamineformaldehyde (30 grams), available commercially as "Uformite MM-83" in 100 grams of water, were added selected reactive $R_f$ additives as seen in Example 17.

The anhydrides were reacted with N,N-dimethylaminoethanol to achieve water solubility as seen in Example 14 and the resin was applied to electrolytic tin plate as described in Example 17. This resin formulation gave 100% wetting of the aqueous phase. Therefore, an additional ionic $R_f$ surfactant was not needed.

The results are tabulated below:

| Ex 19 | Additive = Compound of Example | % of Solids | Coverage after cure | Mol Ratio of COOH/$R_f$ in Additive |
|---|---|---|---|---|
| a | 14a | 0.03 | 65 | 2 |
| b | 14b | 0.03 | 100 | 4 |
| c | 14d | 0.03 | 98 | 2 |
| d | 14c | 0.03 | 65 | 2 |
| e | 14h | 0.03 | 98 | 4 |
| f | 14f | 0.03 | 80 | 2 |
| g | 14e | 0.03 | 50 | 1 |
| h | 14g | 0.03 | 40 | 1 |
| i | 14i | 0.03 | 90 | 4 |
| k | FC-430 | 0.03 | 60 | — |
| l | Control | — | 10 | — |

These results demonstrate the superior performance of the novel $R_f$-additives, with the best results obtained with a high ratio of carboxy/$R_f$ groups.

EXAMPLE 20

A solution of a thermosetting acrylic resin (Rohm & Haas Co.) (50% in xylene) was heated for 10 minutes with 2% (based on total solids) of the compound of Example 1 until a clear solution was obtained. Several films were cast on aluminum panels, dried, and cured 200° C. for 10 minutes, A fluorine-free control sample was also prepared. All samples formed smooth, glossy coatings. Cross-cut adhesion was tested by cutting 5 close lines into the coating with a razor blade, pressing an adhesive tape on the cut and pulling the tape off. If adhesion is unsatisfactory, the coating will strip off. None of the coatings containing the compound of Example 1 failed the test, even when the resin was further diluted to 0.5% additive based on solids.

Control applications, containing no additive, all failed badly.

EXAMPLE 21

453.6 grams of LP-32 polysulfide resin, commercially available from Thiokol, was modified with 6.5 grams (1.4% based on resin) of the dianhydride of Example 1. Samples of modified (T-816F) and unmodified (T-816) LP-32 sealant formulations[1]) were coated on glass, aluminum and concrete and allowed to cure for several days at room temperature. The samples were then cured for an additional 7 days at 70° C. and cut into one inch strips for testing. The samples were then immersed in distilled water at room temperature for 7 days, dried and tested by Instron Testing Apparatus for peel strength. Results are given on Table C.

| 1) | 100 | Parts | LP-32 | |
| | 25 | Parts | CaCO₃ Filler | |
| | 41.5 | Parts | clay | |
| | 10. | Parts | titanium oxide | Part A |
| | 8 | Parts | thixotropic agent | |
| | 0.1 | Part | sulfur | |
| | 23.5 | Parts | plasticizer | |
| | 7.5 | Parts | lead dioxide | |
| | 0.5 | Part | lead stearate | Part B |
| | 4.4 | Parts | plasticizer | |

Parts A and B are mixed together on a roller mill.

Table C

Adhesion of Modified and Unmodified T-816 Polysulfide Sealant to Glass, Aluminum and Concrete

| Substrate | Formulation Test Sample | Average Peel Value lbs. | Type of Failure Adhesive % | Type of Failure Cohesive % |
|---|---|---|---|---|
| aluminum | T-816 a | 21.1 | 20 | 80 |
| | b | 17.7 | 70 | 30 |
| | c | 19.0 | 30 | 70 |
| | d | 20.0 | 50 | 50 |
| | T-816F a | 4.0 | 100 | 0 |
| | b | 5.0 | 100 | 0 |
| | c | 3.0 | 100 | 0 |
| | d | 2.9 | 100 | 0 |
| Glass | T-816 a | 23.0 | 0 | 100 |
| | b | 21.4 | 3 | 97 |
| | c | 22.0 | 0 | 100 |
| | d | 20.2 | 0 | 100 |
| | T-816F a | 13.4 | 100 | 0 |
| | b | 12.5 | 100 | 0 |
| | c | 1.5 | 100 | 0 |
| | d | 2.0 | 100 | 0 |
| Concrete | T-816 a | 0.4 | 100 | 0 |
| | b | — | 100 | 0 |
| | c | 0.7 | 100 | 0 |
| | d | 0.4 | 100 | 0 |
| | T-816F a | 4.0 | 100 | 0 |
| | b | 5.5 | 97 | 3 |
| | c | 2.7 | 100 | 0 |
| | d | 2.5 | 100 | 0 |

On smooth surfaces, such as glass and aluminum, the modified T-816F formulations performs considerably worse than the control. The $R_f$-dianhydride additive acts in fact as an internal mold release agent.

However, on concrete, T816F is considerably better than the control in peel strength values.

EXAMPLE 22

5 g of the dianhydride of Example 1 (33% in ethylene glycol dimethyl ether, glyme) was mixed with 15 g Thanol-TE 3000, a polypropylene oxide (MW: 2000) from Jefferson Chemical Corporation and reacted as described in Example 15. The glyme was evaporated in vacuo at 70° C. This resulting flourine containing prepolymer was used to modify the following two polyurethane foam formulations with varying amounts of fluorine.

| Polyurethane Foam Formulations | | |
|---|---|---|
| | Parts by Weight | |
| Components | A | B |
| Thanol TE-300 | 300 | 300 |
| 1,4-butanediol | 38 | 48 |
| trimethylolpropane | 15 | — |
| water | 0.6 | — |
| T-12 (tin catalyst) | 0.1 | 0.1 |
| Freon 11B | — | 4.2 |
| Isonate 143 L (diisocyanate) | 21 | 19.8 |

The following table shows that very small amounts of fluorine incorporated in this manner greatly reduce the foam density:

| Ex. Number | Formulation | % F | Density [g/cm$^3$] | % by Weight Compound Example 1 in foam |
|---|---|---|---|---|
| 1 | A | — | 0.39 | 0 |
| 2 | A | 0.0021 | 0.29 | 0.00534 |
| 3 | A | 0.0042 | 0.24 | 0.01068 |
| 4 | A | 0.0084 | 0.22 | 0.02136 |
| 5 | A | 0.0168 | 0.23 | 0.04272 |
| 6 | B | 0 | 0.48 | 0 |
| 7 | B | 0.002 | 0.39 | 0.0051 |
| 8 | B | 0.004 | 0.34 | 0.0102 |
| 9 | B | 0.008 | 0.31 | 0.0204 |
| 10 | B | 0.016 | 0.28 | 0.0408 |

EXAMPLE 23

5 g of the dianhydride of Example 1 (33% in glyme) was mixed with 15 g of two different siloxane diols of the following structures:

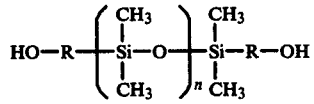

Available from Dow Corning under the Code Nr. Q4-3667

MW: 2400    n = approximately 30

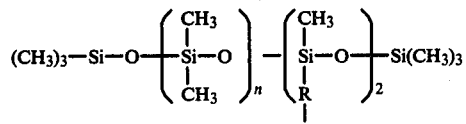

Available from Dow Corning under Code Nr. Q4-3557

(MW: 800)    n = approximately 6.

R is a lower alkylene of up to 6 carbons.

The mixtures are heated to 100° C. and stirred for 20 minutes, after which time clear solutions were obtained, which consisted of the siloxane - diesters with the novel dianhydride, dissolved in excess siloxane diol.

Solutions of Silicone DC-20 (Dow Corning Corporation), 6% in 1,1,1,-trichloroethane, a mold release agent used in polyurethane manufacture, were modified by small amounts of the above prepared derivatives to give 0.4% F. on solids and tested for their wetting behavior on aluminum sheet by spreading a thin film with a Nr. 20 wire rod.

Excellent wetting was achieved with both additives, while the control sample beaded up. In addition, the sample derived from Q4-3557 showed very little foaming.

What is claimed is:

1. A method for improving the coating of substrates by a water based coating formulation of a water soluble, crosslinkable resin containing polyethylene oxide segments as water solubilizing units and being derived from diepoxides, said formulation containing an ionic fluorinated surfactant, which comprises adding an effective amount of a watersoluble or water-dispersible, resin-compatible product obtained by reacting (a) an R$_f$ containing anhydride of the formula I

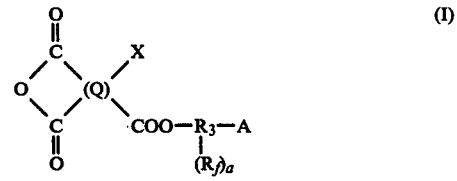

wherein

Q is a tetraradical of a tricarboxylic or tetracarboxylic acid selected from the group consisting of trimellitic acid, 3,3′,4,4′-benzophenonetetracarboxylic acid and 1,2,4,5-benzenetetracarboxylic acid, X is hydrogen or carboxy;

R$_f$ is perfluoroalkyl of 6 to 18 carbon atoms;

a is 1 or 2;

A is hydrogen or group II;

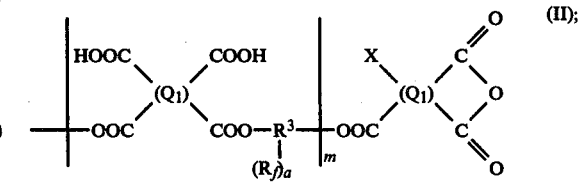

m is O;

Q$_1$ is the same as Q, and

R$_3$ is the residue of an R$_f$ substituted aliphatic alcohol or diol of the structure

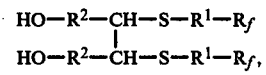

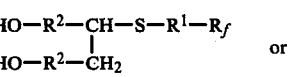

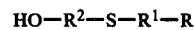

where R$_1$ is a branched or straight chain alkylene of 1 to 12 carbon atoms, alkylenethioalkylene of 4 to 12 carbon atoms, alkyleneoxyalkylene of 4 to 12 carbon atoms or alkyleneiminoalkylene of 4 to 12 carbon atoms where the nitrogen atom contains as the third substituent hydrogen or alkyl of 1 to 6 carbon atoms; and R$_2$ is straight or branched chain alkylene of 1 to 12 carbon atoms or an alkylenepolyoxyalkylene of the formula C$_n$H$_{2n}$COC$_k$H$_{2k}$)$_r$ where n is 1 or 12, k is 2 to 6 and r is 1 to 40; with (b) a tertiary amine containing compound selected from the group consisting of N,N-dimethylaminoethanol; N-methyldiethanolamine; 3;1-dimethylamino-1-propanol; 1-dimethylamino-2-propanol; and N,N-bis(2-hydroxypropyl)aniline; in the ratio of one mole of the tertiary amine containing compound (b) used for each mole of anhydride group of R$_f$ containing compound (a); with the mol ratio of carboxy/R$_f$ groups in the product being 1 to 4; to said formulation.

to 4; to said formulation.

2. A method according to claim 1 wherein the effective amount of the water soluble or water dispersible product is from 0.03 to 0.2% by weight of solids.

3. A method according to claim 1 wherein the ionic surfactant is amphoteric fluorinated surfactant.

4. A method according to claim 1 where in the R$_f$ containing anhydride of formula I Q is the tetraradical of 3,3',4,4'-benzophenonetetracarboxylic acid; X is carboxy; R$_f$ is perfluoroalkyl of 6 to 18 carbon atoms; a is 1 or 2; A is group II

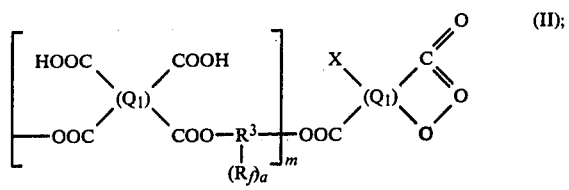

m is 0; Q$_1$ is the same as Q and

R$^3$ is the residue of an R$_f$ substituted aliphatic alcohol or diol of the structure

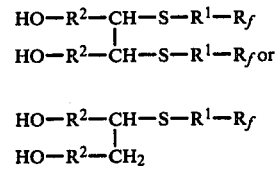

where R$^1$ is a branched or straight chain alkylene of 1 to 4 carbon atoms; and R$^2$ is a branched or straight chain alkylene of 1 to 4 carbon atoms or alkylenepolyoxyalkylene of the formula C$_n$H$_{2n}$(OC$_k$H$_{2k}$)$_r$ where n is 1 to 4, k is 2 to 4 and r is 1 to 20.

5. A method according to claim 4 wherein the R$_f$ containing anhydride of formula I R$^1$ is ethylene; and R$_2$ is methylene or methylenepolyoxyalkylene of the formula CH$_2$(OC$_k$H$_{2k}$)$_r$ where k is 2 and r is 1 to 20.

6. A method according to claim 1 wherein the tertiary amine containing compound (b) is N,N-dimethylaminoethanol.

7. A method according to claim 1 wherein the R$_f$ containing anhydride has the structure

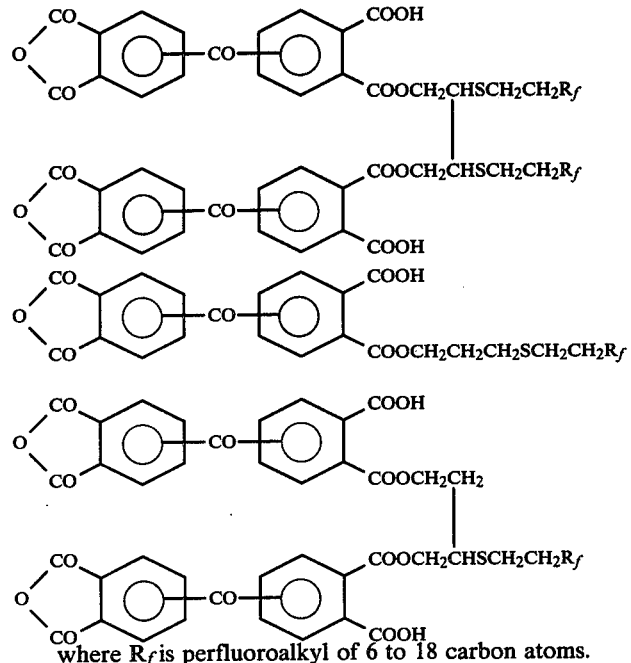

where R$_f$ is perfluoroalkyl of 6 to 18 carbon atoms.

8. A method according to claim 7 wherein the tertiary amine containing compound (b) is N,N-dimethylaminoethanol.

9. A method according to claim 1 wherein the mol ratio of carboxy/R$_f$ groups in the product obtained by reacting (a) with (b) is 2 to 4.

* * * * *

UNITED STATES PATENT AND TRADEMARK OFFICE
CERTIFICATE OF CORRECTION

PATENT NO. : 4,153,590
DATED : May 8, 1979
INVENTOR(S) : Karl Friedrich Mueller

It is certified that error appears in the above-identified patent and that said Letters Patent are hereby corrected as shown below:

Claim 1, column 31, line 7 delete "$C_nH_{2n}COC_kH_{2k})_r$" and insert:

$$--C_nH_{2n}(OC_kH_{2k})_r--$$

Signed and Sealed this

Twenty-ninth Day of January 1980

[SEAL]

Attest:

SIDNEY A. DIAMOND

Attesting Officer

Commissioner of Patents and Trademarks